(12) United States Patent
Yamana et al.

(10) Patent No.: US 9,354,164 B2
(45) Date of Patent: May 31, 2016

(54) OPTICAL SYSTEM, TERAHERTZ EMISSION MICROSCOPE, AND METHOD OF MANUFACTURING A DEVICE

(71) Applicant: Sony Corporation, Tokyo (JP)

(72) Inventors: Hiroaki Yamana, Kanagawa (JP); Masanao Kamata, Tokyo (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 14/268,768

(22) Filed: May 2, 2014

(65) Prior Publication Data

US 2014/0332687 A1    Nov. 13, 2014

(30) Foreign Application Priority Data

May 9, 2013   (JP) .................... 2013-099245

(51) Int. Cl.

| G01N 21/31 | (2006.01) |
|---|---|
| *G01N 21/3581* | (2014.01) |
| *G01N 21/3586* | (2014.01) |
| G03F 1/84 | (2012.01) |
| G01B 9/04 | (2006.01) |
| G01J 3/42 | (2006.01) |

(52) U.S. Cl.
CPC ........ *G01N 21/3581* (2013.01); *G01N 21/3586* (2013.01); *G01B 9/04* (2013.01); *G01J 3/42* (2013.01); *G03F 1/84* (2013.01)

(58) Field of Classification Search
CPC .......... G01N 21/3581; G01N 21/3586; G01N 21/31; G01N 21/3563; G01N 21/3568; G01N 21/62; G01N 21/63; G01B 9/04; G02B 21/0096; G02B 21/02; G02B 21/06; G02B 21/361; H01Q 15/02; H01Q 15/16; H01P 3/127; H01P 5/00; G03F 1/84

See application file for complete search history.

(56) References Cited

U.S. PATENT DOCUMENTS

| 7,315,175 B2* | 1/2008 | Cole ............................... 850/56 |
|---|---|---|
| 7,406,151 B1* | 7/2008 | Yun et al. ........................ 378/43 |
| 2002/0021868 A1* | 2/2002 | Mandella ........................ 385/34 |
| 2004/0257576 A1* | 12/2004 | Kirsch et al. .................. 356/436 |
| 2006/0022141 A1* | 2/2006 | Zhang et al. ............... 250/341.1 |

FOREIGN PATENT DOCUMENTS

JP    2006-156978    6/2006

OTHER PUBLICATIONS

Tonouchi et al., "Laser Terahertz Emission Microscope," Terahertz Science and Technology, vol. 1, No. 1, Mar. 2008 (pp. 36)28-36.*

* cited by examiner

*Primary Examiner* — Yara B Green
(74) *Attorney, Agent, or Firm* — Dentons US LLP

(57) ABSTRACT

There is provided an optical system, including: an extracting section, the refractive index of the extracting section being approximately the same as the refractive index of an observed object, the extracting section being optically coupled with the observed object to thereby extract a terahertz electromagnetic wave generated from the observed object; and an ellipsoidal reflector surface having a first focal point and a second focal point, the observed object being to be arranged on the first focal point, a photoconductive device being on the second focal point, the photoconductive device being configured to detect the terahertz electromagnetic wave extracted by the extracting section, the ellipsoidal reflector surface guiding the extracted terahertz electromagnetic wave to the photoconductive device.

20 Claims, 13 Drawing Sheets

OPTICAL SYSTEM, TERAHERTZ EMISSION MICROSCOPE, AND METHOD OF MANUFACTURING A DEVICE

CROSS REFERENCE TO RELATED APPLICATIONS

This application claims the benefit of Japanese Priority Patent Application JP 2013-099245 filed Mar. 14, 2013, the entire contents of which are incorporated herein by reference.

BACKGROUND

The present disclosure relates to a terahertz emission microscope, which makes use of terahertz electromagnetic waves. The present disclosure further relates to a photoconductive device and a lens, which are used in the terahertz emission microscope. The present disclosure further relates to a method of manufacturing a device. The method includes observing the device by using the terahertz emission microscope.

Japanese Patent Application Laid-open No. 2006-156978 discloses a system of manufacturing a semiconductor apparatus. The system employs a method of inspecting a semiconductor device contactlessly. The method makes use of terahertz electromagnetic waves. According to this inspection method, an excitation pulsed laser (e.g., ultrashort pulsed laser, etc.) is irradiated on a semiconductor device, i.e., an examined object. Then the semiconductor device generates terahertz electromagnetic waves. The terahertz electromagnetic waves are affected by an electric field distribution and defective wiring of the semiconductor device. The inspection method makes use of this phenomenon in inspecting defects in semiconductor devices.

A built-in electric field is generated in a p-n junction of a MOS (Metal Oxide Semiconductor) transistor, the surface of a metal semiconductor, and the like of a semiconductor device, even under a no-bias voltage. Because of this, according to such an inspection method, which makes use of terahertz electromagnetic waves, it is possible to inspect defects under a no-bias condition, i.e., contactlessly.

SUMMARY

What is required for such an inspection method, which makes use of terahertz electromagnetic waves, is to detect terahertz electromagnetic waves generated from semiconductor devices with a high degree of accuracy. Let's say that terahertz electromagnetic waves generated from semiconductor devices are weak, and that the efficiency of collecting light on a detection device is low. In those cases and other cases, the accuracy of detecting terahertz electromagnetic waves is decreased.

In view of the above-mentioned circumstances, it is desirable to provide a terahertz emission microscope with which the accuracy of detecting terahertz electromagnetic waves is increased. It is further desirable to provide an optical system used in the terahertz emission microscope, and a method of manufacturing a device.

According to an embodiment of the present technology, there is provided an optical system, including: an extracting section, the refractive index of the extracting section being approximately the same as the refractive index of an observed object, the extracting section being optically coupled with the observed object to thereby extract a terahertz electromagnetic wave generated from the observed object; and an ellipsoidal reflector surface having a first focal point and a second focal point, the observed object being to be arranged on the first focal point, a photoconductive device being on the second focal point, the photoconductive device being configured to detect the terahertz electromagnetic wave extracted by the extracting section, the ellipsoidal reflector surface guiding the extracted terahertz electromagnetic wave to the photoconductive device.

According to the optical system, the extracting section is optically coupled with the observed object. The extracting section extracts the terahertz electromagnetic wave generated from the observed object. Further, the ellipsoidal reflector surface guides the terahertz electromagnetic wave from the observed object to the photoconductive device. The observed object is on the first focal point. The photoconductive device is on the second focal point. As a result, the efficiency of extracting the terahertz electromagnetic wave is increased, and the efficiency of collecting light on the photoconductive device is increased. As a result, the accuracy of detecting the terahertz electromagnetic wave may be increased.

The observed object may be an observed device.

It is possible to, for example, inspect defects in a device with a high degree of accuracy.

The extracting section may be a first solid immersion lens, the first solid immersion lens including an extracting surface and an output surface, the extracting surface being flat, the extracting surface being adjacent to or abutting on the device, the output surface being curved, the output surface outputting the extracted terahertz electromagnetic wave, and the ellipsoidal reflector surface may be an ellipsoidal mirror.

As described above, the first solid immersion lens may be used as the extracting section. The first solid immersion lens includes the flat extracting surface and the curved output surface. Because of this, it is possible to extract and output the terahertz electromagnetic wave efficiently. Further, because the ellipsoidal mirror is used, the light-collecting efficiency is increased.

The optical system may further include a light-collecting section, the refractive index of the light-collecting section being approximately the same as the refractive index of the photoconductive device, the light-collecting section being optically coupled with the photoconductive device to thereby collect the terahertz electromagnetic wave on the photoconductive device, the terahertz electromagnetic wave being guided by the ellipsoidal reflector surface.

The optical system includes the light-collecting section. The light-collecting section is optically coupled with the photoconductive device. The light-collecting section may increase the light-collecting efficiency and the accuracy of detecting the terahertz electromagnetic wave.

The light-collecting section may be a second solid immersion lens, the second solid immersion lens including an entrance surface and a coupling surface, the entrance surface being curved, the terahertz electromagnetic wave entering the entrance surface, the terahertz electromagnetic wave being guided by the ellipsoidal reflector surface, the coupling surface being flat, the coupling surface being adjacent to or abutting on the photoconductive device.

As described above, the second solid immersion lens may be used as the light-collecting section. The second solid immersion lens includes the curved entrance surface and the flat coupling surface. Because of this, it is possible to collect the terahertz electromagnetic wave efficiently.

A reflector film member may be formed on the ellipsoidal mirror, the reflector film member reflecting the terahertz electromagnetic wave.

Because of this, the efficiency of collecting the terahertz electromagnetic wave may be increased.

The ellipsoidal mirror may be made of a material reflecting the terahertz electromagnetic wave.

Because of this, the efficiency of collecting the terahertz electromagnetic wave may be increased. Further, the number of parts may be reduced.

The extracting section may extract the terahertz electromagnetic wave, the terahertz electromagnetic wave being generated in a case where a pulsed laser is irradiated on the device, and a first film member may be formed on the extracting surface of the first solid immersion lens, the first film member transmitting the terahertz electromagnetic wave and reflecting the pulsed laser.

Because of this, generation of the terahertz electromagnetic wave, which results from the pulsed laser entering the first solid immersion lens, may be suppressed. As a result, the accuracy of detecting the terahertz electromagnetic wave, which is generated from the observed device, may be increased.

A second film member may be formed on the entrance surface of the second solid immersion lens, the second film member transmitting the terahertz electromagnetic wave and reflecting the pulsed laser.

Because of this, generation of the terahertz electromagnetic wave, which results from the pulsed laser entering the second solid immersion lens or the photoconductive device, may be suppressed. As a result, the accuracy of detecting the terahertz electromagnetic wave, which is generated from the observed device, may be increased.

The distance between the extracting surface of the first solid immersion lens and the device may be 1 mm or less.

Because of this, the terahertz electromagnetic wave may be extracted sufficiently.

The distance between the coupling surface of the second solid immersion lens and the photoconductive device may be 1 mm or less.

Because of this, the terahertz electromagnetic wave may be collected sufficiently.

The extracting section may be an ellipsoidal lens, the ellipsoidal lens including a first surface, the first surface being flat, the first surface being adjacent to or abutting on the device, and the ellipsoidal reflector surface may be a second surface of the ellipsoidal lens, the second surface being ellipsoidal.

As described above, the extracting section may be an ellipsoidal lens, and the ellipsoidal reflector surface may be an ellipsoidal lens. Also with this structure, the efficiency of extracting the terahertz electromagnetic wave, the light-collecting efficiency, and the detection accuracy may be increased.

The optical system may further include a coupling surface being optically coupled with the photoconductive device to thereby collect the terahertz electromagnetic wave on the photoconductive device, the terahertz electromagnetic wave being guided by the second surface, the coupling surface being a third surface of the ellipsoidal lens, the third surface being flat, the third surface being adjacent to or abutting on the photoconductive device.

Because of this, the efficiency of collecting the terahertz electromagnetic wave may be increased.

A reflector film member may be formed on the second surface, the reflector film member reflecting the terahertz electromagnetic wave.

Because of this, the efficiency of collecting the terahertz electromagnetic wave may be increased.

The extracting section may extract the terahertz electromagnetic wave, the terahertz electromagnetic wave being generated in a case where a pulsed laser is irradiated on the device, and a film member may be formed on the first surface, the film member transmitting the terahertz electromagnetic wave and reflecting the pulsed laser.

Because of this, generation of the terahertz electromagnetic wave, which results from the pulsed laser entering the ellipsoidal lens, may be suppressed. As a result, the accuracy of detecting the terahertz electromagnetic wave, which is generated from the observed device, may be increased.

The distance between the first surface and the device may be 1 mm or less, and the distance between the third surface and the photoconductive device may be 1 mm or less.

Because of this, the terahertz electromagnetic wave may be extracted and collected on the photoconductive device sufficiently.

The extracting section may include a first solid immersion lens, the first solid immersion lens including an extracting surface and an output surface, the extracting surface being flat, the extracting surface being adjacent to or abutting on the device, the output surface being curved, the output surface outputting the extracted terahertz electromagnetic wave, the ellipsoidal reflector surface being an ellipsoidal surface of an ellipsoidal lens, the ellipsoidal lens including a first mounting portion, the first solid immersion lens being mounted on the first mounting portion.

As described above, the extracting section and the ellipsoidal reflector surface may be the combination of the first solid immersion lens and the ellipsoidal lens. Also with this structure, the efficiency of extracting the terahertz electromagnetic wave, the light-collecting efficiency, and the detection accuracy may be increased.

The optical system may further include a second solid immersion lens, the second solid immersion lens including an entrance surface and a coupling surface, the terahertz electromagnetic wave entering the entrance surface, the terahertz electromagnetic wave being guided by the ellipsoidal surface, the coupling surface being flat, the coupling surface being adjacent to or abutting on the photoconductive device, the second solid immersion lens being mounted on a second mounting portion, the second mounting portion being formed on the ellipsoidal lens.

As described above, the second solid immersion lens, which is optically coupled with the photoconductive device, may be further used. The second solid immersion lens is mounted on the second mounting portion. The second mounting portion is formed on the ellipsoidal lens.

Because of this, the efficiency of collecting the terahertz electromagnetic wave may be increased.

The first refractive index of the first solid immersion lens may be approximately the same as the refractive index of the device, and the second refractive index of the second solid immersion lens may be approximately the same as the refractive index of the photoconductive device.

As described above, the refractive index of the first lens is set arbitrarily, and the refractive index of the second lens is set arbitrarily. Because of this, the efficiency of extracting the terahertz electromagnetic wave may be increased, and the light-collecting efficiency may be increased.

According to another embodiment of the present technology, there is provided a terahertz emission microscope, including: a light source configured to generate a pulsed laser; a photoconductive device configured to detect a terahertz electromagnetic wave, the terahertz electromagnetic wave being generated in a case where the pulsed laser is irradiated on an observed object; an extracting section, the refractive index of the extracting section being approximately the same as the refractive index of the observed object, the extracting section being optically coupled with the observed object to thereby extract a terahertz electromagnetic wave generated from the observed object; and an ellipsoidal reflector surface having a first focal point and a second focal point, the observed object being to be arranged on the first focal point, the photoconductive device being on the second focal point, the ellipsoidal reflector surface guiding the extracted terahertz electromagnetic wave to the photoconductive device.

The light source may be configured to irradiate the pulsed laser on the observed object, whereby the observed object generates a terahertz electromagnetic wave having a frequency of 1010 (Hz) or more and 1014 (Hz) or less.

The light source may be configured to generate a pulsed laser having a wavelength of 2 μm or less and having a pulse width of 100 ps or less.

According to another embodiment of the present technology, there is provided a method of manufacturing a device, the method including inspecting a defect in the device by using a terahertz emission microscope, the method including: generating a pulsed laser from a light source; optically coupling an extracting section with the device to thereby extract the terahertz electromagnetic wave generated from the device, the refractive index of the extracting section being approximately the same as the refractive index of the device; guiding, by an ellipsoidal reflector surface, the extracted terahertz electromagnetic wave from the device to a photoconductive device, the ellipsoidal reflector surface having a first focal point and a second focal point, the device being on the first focal point, the photoconductive device being on the second focal point; and detecting, by the photoconductive device, the terahertz electromagnetic wave.

As described above, according to the present technology, the accuracy of detecting terahertz electromagnetic waves may be increased.

These and other objects, features and advantages of the present disclosure will become more apparent in light of the following detailed description of best mode embodiments thereof, as illustrated in the accompanying drawings.

DETAILED DESCRIPTION OF EMBODIMENTS

Hereinafter, embodiments of the present disclosure will be described with reference to the drawings.
<First Embodiment>
[Structure of Terahertz Emission Microscope]

Figure 1:
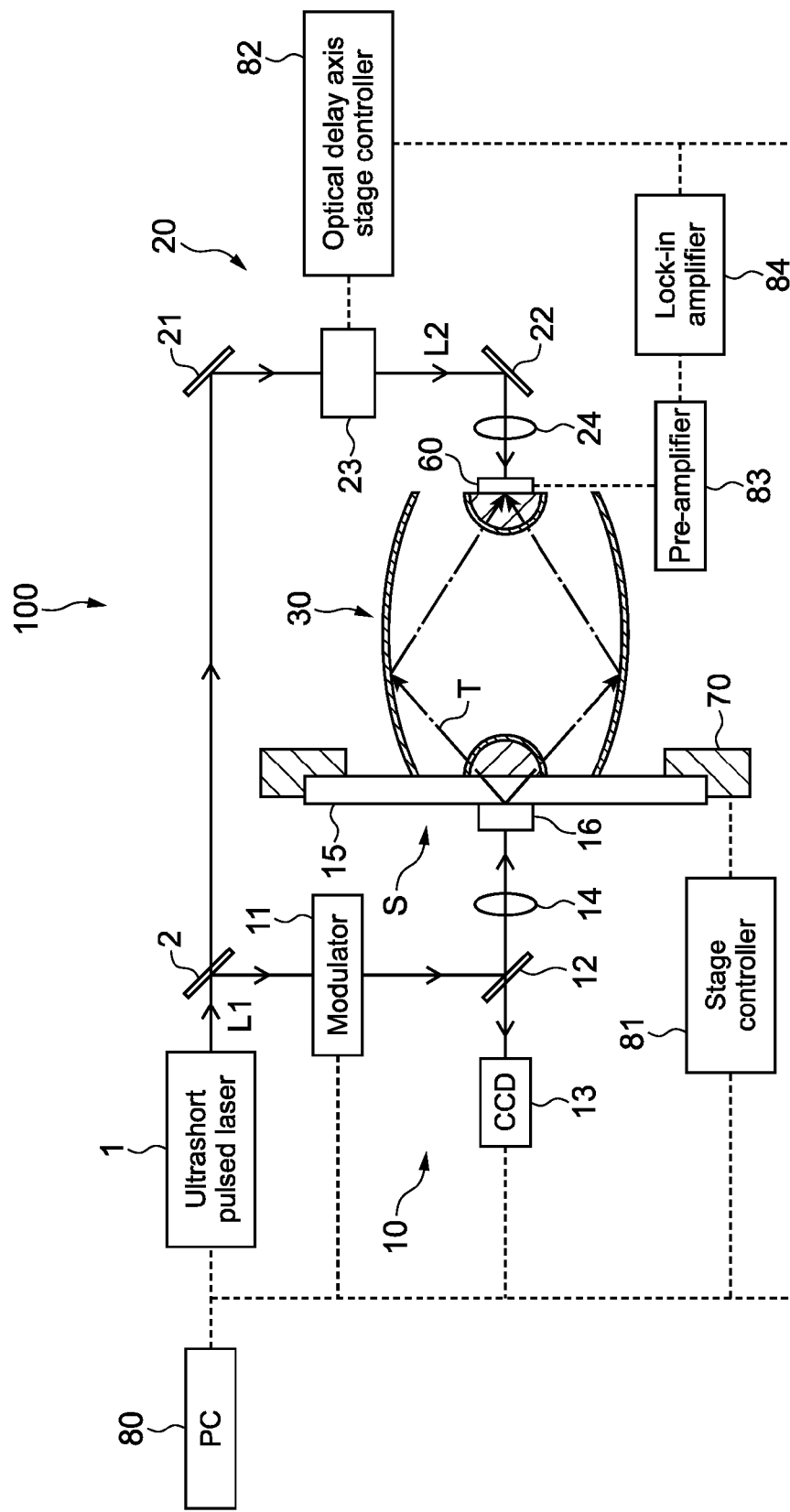
FIG. 1 is a diagram schematically showing the structure of a terahertz emission microscope of the first embodiment.

FIG. 1 is a diagram schematically showing the structure of a terahertz emission microscope of the first embodiment of the present technology. The terahertz emission microscope 100 includes the excitation light source 1, the half mirror 2, the first irradiation optical system 10, the second irradiation optical system 20, the light-guiding optical system 30, the photoconductive device 60, and the stage 70.

The excitation light source 1 is a light source, which is configured to generate pulsed laser for excitation. The pulsed laser excites an observed object, which is mounted on the stage 70. Here, the observed object is a device, which is an examined object (hereinafter referred to as "object device S".). The excitation light source 1 generates pulsed laser. For example, the excitation light source 1 generates ultrashort pulsed laser, which has a wavelength of 2 μm or less and a width of 100 ps or less.

The half mirror 2 reflects a part of pulsed laser L1, which is generated from the excitation light source 1. The half mirror 2 guides the reflected light to the first irradiation optical system 10. Further, the half mirror 2 transmits a part of the pulsed laser. The pulsed laser enters the second irradiation optical system 20.

The first irradiation optical system 10 includes the intensity modulator 11, the half mirror 12, the image-extracting section 13, and the condenser lens 14. The structures thereof are not specifically limited. For example, the intensity modulator 11 is an optical chopper or the like. The image-extracting section 13 is a CCD (Charge-Coupled Device) or the like. The half mirror 2 reflects the pulsed laser L1. The pulsed laser L1 passes through the intensity modulator 11. The half mirror 12 reflects the pulsed laser L1. The pulsed laser L1 enters the condenser lens 14. The condenser lens 14 guides the pulsed laser L1 to the object device S on the stage 70.

The pulsed laser L1 is irradiated on the object device S. Then, the object device S generates the terahertz wave T. For example, the frequency of the terahertz wave T is 1010 (Hz) or more and 1014 (Hz) or less. Specifically, the pulsed laser enters the object device S. Then, free electron emerges in the object device S. The internal electric field of the object device S accelerates the free electron. As a result, transient current occurs. The transient current generates dipole radiation. As a result, terahertz electromagnetic wave (hereinafter referred to as "terahertz wave T") is radiated. Note that the wavelength of the terahertz wave T is not limited to the above-mentioned wavelength range.

Typically, the object device S is a semiconductor device, which is mainly made of a semiconductor material. For example, the object device S is a light-emitting device such as a semiconductor laser or a light-emitting diode. In this embodiment, the semiconductor devices 16 are mounted on the plate 15. The terahertz wave T is detected under this state. That is, the object device S includes the entire plate 15 and the semiconductor devices 16. As shown in FIG. 1, the stage 70 holds the plate 15. The stage 70 moves under this state. Because of this, the object device S may move to a predetermined examination position.

The half mirror 12 partially transmits light, and guides the light to the image-extracting section 13. A user may confirm if the pulsed laser L1 is irradiated on the predetermined position. In this embodiment, the plurality of semiconductor devices 16 are mounted on the plate 15. The pulsed laser L1 is irradiated on the plate 15. At this time, the user may confirm if the pulsed laser L1 is irradiated on the predetermined semiconductor device 16.

The second irradiation optical system 20 includes the two reflector mirrors 21 and 22, the optical delay path 23, and the condenser lens 24. Pulsed laser enters the second irradiation optical system 20. The reflector mirror 21 reflects the pulsed laser. The pulsed laser enters the optical delay path 23. The optical delay path 23 generates sampling pulsed laser L2. The photoconductive device 60 uses the sampling pulsed laser L2 to detect the terahertz wave T at the arbitrary timing. The sampling pulsed laser L2, which is generated from the optical delay path 23, enters the photoconductive device 60 via the reflector mirror 22 and the condenser lens 24.

Typically, the optical delay path 23 uses a movement mechanism or the like, which is configured to move a mirror (not shown). The optical delay path 23 variably controls the optical-path length of the pulsed laser, which has regular intervals. In this embodiment, a single-axis stage, a retroreflector, and the like are used. The single-axis stage is caused to move. As a result, the optical-path length is controlled. The arrival time of the pulsed laser at the photoconductive device 60 also changes depending on the optical-path length. As a result, the optical delay path 23 may output the sampling pulsed laser L2 at the predetermined timing. The output timing of the sampling pulsed laser L2 is controlled. Because of this, the detection timing of the terahertz wave T is controlled. As a result, the time waveform of the electric field intensity of the terahertz wave T may be obtained.

The light-guiding optical system 30 is an optical system configured to guide the terahertz wave T, which is generated from the object device S, to the photoconductive device 60. The light-guiding optical system 30 will be described in detail later.

The photoconductive device 60 is also referred to as photoconductive antenna (PCA). The photoconductive device 60 has a structure capable of detecting the terahertz wave T. The structure of the photoconductive device 60 may be known. For example, the photoconductive device 60 includes the plate 61 as a base material and the electrodes 62 (see FIG. 4). The electrodes 62 are formed on the plate 61. The electrodes 62 are arranged independently such that there is a small gap between the electrodes 62. The electrodes 62 are arranged such that the electrodes 62 form an antenna. Further, a photoconductive film (not shown) is formed on the plate 61. Excitation light is irradiated on the photoconductive film. Then photocarrier is generated. Typically, the plate 61 is made of a GaAs-based semiconductor material. Alternatively, the plate 61 may be made of another material. The electrodes 62 are formed on the surface 63 of the plate 61. The above-mentioned sampling pulsed laser L2 enters the surface 63.

The terahertz wave T from the object device S enters a surface different from the surface 63, i.e., the entrance surface 64. In this embodiment, the entrance surface 64 is the opposite side of the surface 63.

The current flowing between the electrodes 62 (or voltage between the electrodes 62) changes depending on the amplitude of the terahertz wave T, which is generated from the object device S. When the terahertz wave T enters the gap between the electrodes 62 on the plate 61, the terahertz emission microscope 100 measures the current (or voltage) between the electrodes 62 at the timing when the sampling pulsed laser L2 enters the photoconductive device 60. As a result, the terahertz emission microscope 100 may obtain amplitude values of the terahertz wave T every time the sampling pulsed laser L2 enters the photoconductive device 60, in waveform.

Further, as shown in FIG. 1, the terahertz emission microscope 100 includes the controller 80, the stage controller 81, the optical delay axis stage controller 82, the pre-amplifier 83, and the lock-in amplifier 84. The stage controller 81 controls movement of the stage 70. The optical delay axis stage controller 82 controls movement of a single-axis stage. The single-axis stage is configured to delay the optical-path length. The pre-amplifier 83 is configured to amplify current, which is obtained by the photoconductive device 60. The lock-in amplifier 84 is configured to lock-in detect a signal by using an input signal having the modulation frequency, which is obtained by the intensity modulator 11. The controller 80 controls the intensity modulator 11, the image-extracting section 13, the stage controller 81, the optical delay axis stage controller 82, the pre-amplifier 83, and the lock-in amplifier 84. The controller 80 may be, for example, a PC or the like. Alternatively, the controller 80 may be a control block including a CPU, a ROM, and the like.

[Structure of Light-Guiding Optical System]

Figure 2:
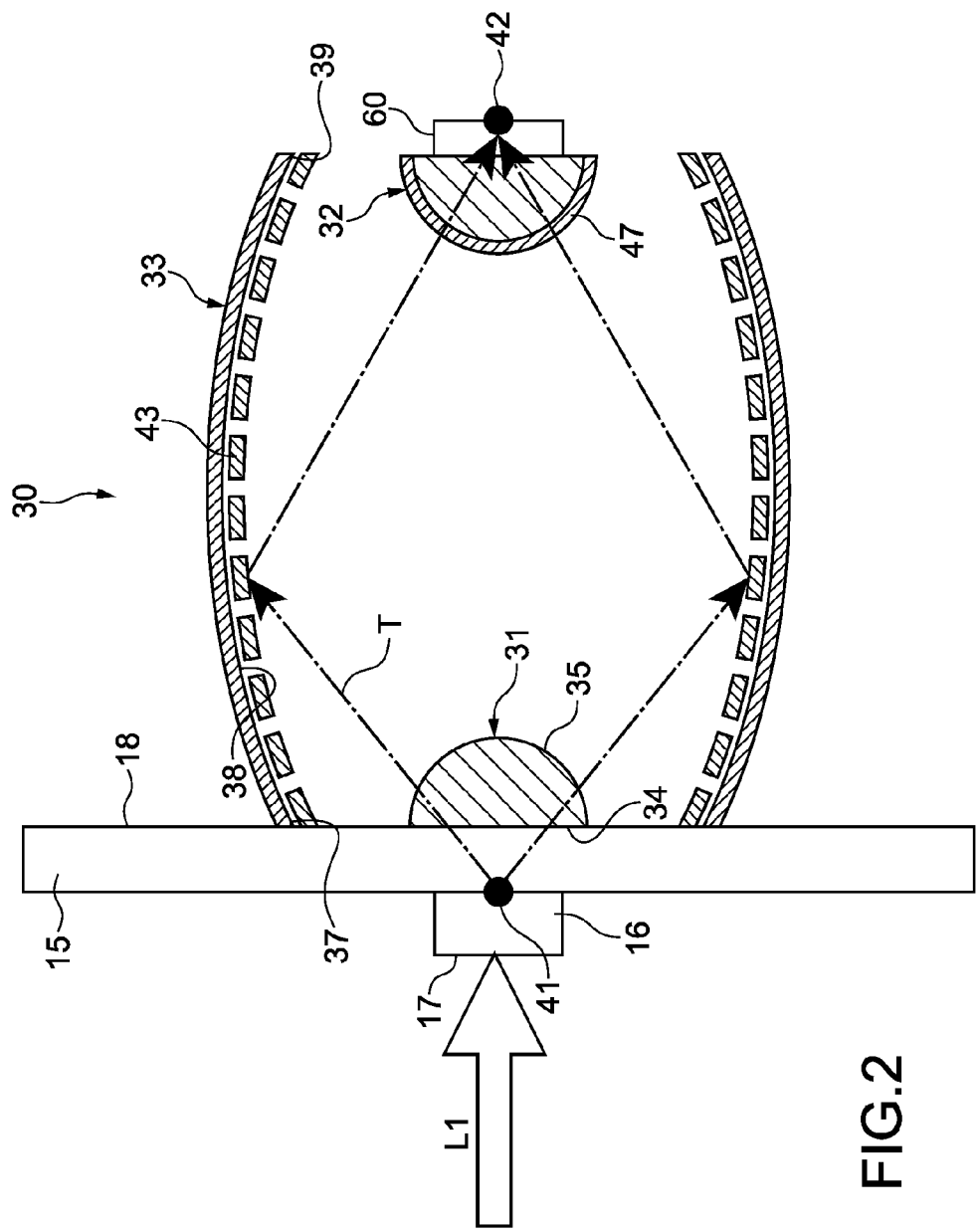
FIG. 2 is a diagram schematically showing the structure of a light-guiding optical system of this embodiment.
Figure 3:
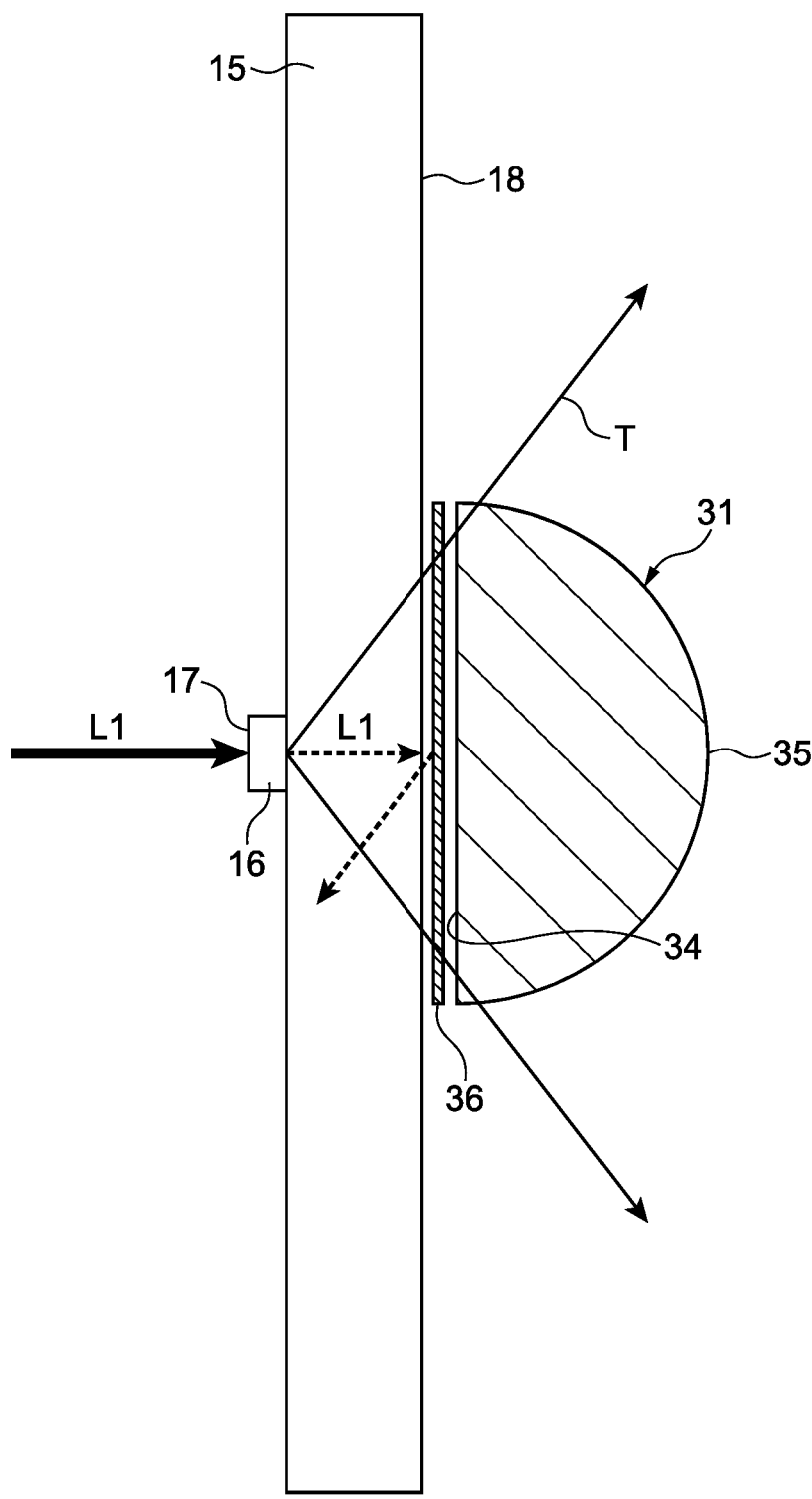
FIG. 3 is a diagram showing the enlarged first solid immersion lens of FIG. 2.
Figure 4:
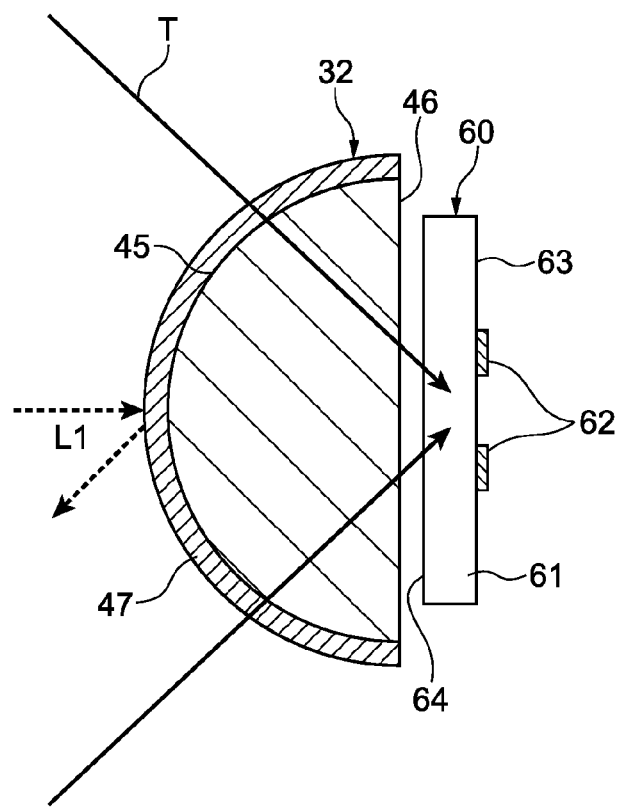
FIG. 4 is a diagram showing the enlarged second solid immersion lens of FIG. 2.

FIG. 2 is a diagram schematically showing the structure of the light-guiding optical system 30 of this embodiment. FIG. 3 is a diagram showing the enlarged first solid immersion lens 31 of FIG. 2. FIG. 4 is a diagram showing the enlarged second solid immersion lens 32 of FIG. 2. The light-guiding optical system 30 includes the first solid immersion lens 31, the second solid immersion lens 32, and the ellipsoidal mirror 33. The ellipsoidal mirror 33 is arranged such that the ellipsoidal mirror 33 surrounds the first solid immersion lens 31 and the second solid immersion lens 32.

In this embodiment, the refractive index of the first solid immersion lens 31 is approximately equal to the refractive index of the object device S, i.e., the observed object. The first solid immersion lens 31 is optically coupled with the object device S. As a result, the first solid immersion lens 31 extracts the terahertz wave T, which is generated from the object device S. In short, the first solid immersion lens 31 plays a role of an extracting section.

Here, the "refractive index" means the refractive index of the terahertz electromagnetic waveband. Further, the phrase "the refractive index approximately equal to the refractive index of the object device S" means the refractive index approximately equal to the refractive index of a part of the first solid immersion lens 31, which extracts the terahertz wave T. As shown in FIG. 2, in this embodiment, the pulsed laser L1 is irradiated on the front surface 17 side of the semiconductor device 16.

The terahertz wave T is extracted from the back surface 18 side of the plate 15. That is, a part from which the terahertz wave T is extracted is the back surface 18 of the plate 15. The refractive index approximately equal to the refractive index of the object device S is the refractive index approximately equal to the refractive index of the plate 15.

Further, the phrase "the first solid immersion lens 31 is optically coupled with the object device S" means that the first solid immersion lens 31 is near-field coupled with or abuts on the object device S. That is, the phrase means that, when the first solid immersion lens 31 is adjacent to the object device S, the first solid immersion lens 31 is capable of extracting the terahertz wave T as near-field light (evanescent light). Alternatively, the phrase means that, when the first solid immersion lens 31 abuts on the object device S, the first solid immersion lens 31 is capable of extracting the terahertz wave T, which is generated from the object device S, as it is. In the description, the phrase "to be optically coupled with" conceptually includes those two statuses.

The first solid immersion lens 31 includes the extracting surface 34 and the output surface 35. The extracting surface 34 is flat. The extracting surface 34 is adjacent to or abuts on the object device S. The output surface 35 is curved. The output surface 35 outputs the terahertz wave T, which is extracted at the extracting surface 34. The first solid immersion lens 31 may be made of any material. For example, the first solid immersion lens 31 is made of a semiconductor such as Si or Ge, or a dielectric material such as $Al_2O_3$ or $SiO_2$. The material may be selected arbitrarily such that the refractive index of the terahertz electromagnetic waveband is approximately equal to the refractive index of the plate 15.

The first solid immersion lens 31 may have any shape. The first solid immersion lens 31 may be designed arbitrarily. The first solid immersion lens 31 may be designed arbitrarily based on the size or the thickness of each of the semiconductor device 16, the size or the thickness of the plate 15 (the object device S includes the plate 15 and semiconductor devices 16), the size or the curvature of the ellipsoidal mirror 33 (described below), the distance between the first solid immersion lens 31 and the photoconductive device 60, or the like. The curved output surface 35 may not be a hemisphere. The curved output surface 35 may be a part of a hemisphere, aspheric, a fresnel lens, or the like. In this embodiment, the first solid immersion lens 31 has the flat extracting surface 34 and the curved output surface 35. Because of this, the first solid immersion lens 31 is capable of extracting and outputting the terahertz wave T efficiently.

In this embodiment, the distance between the extracting surface 34 of the first solid immersion lens 31 and the back surface 18 of the plate 15 is 1 mm or less. Because of this, the first solid immersion lens 31 is capable of extracting the terahertz wave T sufficiently. This value is based on the wavelength of the terahertz electromagnetic waveband. However, the distance between the extracting surface 34 of the first solid immersion lens 31 and the back surface 18 of the plate 15 may not be 1 mm or less. The distance between the extracting surface 34 of the first solid immersion lens 31 and the back surface 18 of the plate 15 may be determined arbitrarily as long as the first solid immersion lens 31 is capable of extracting the terahertz wave T.

As shown in FIG. 3, the first film member 36 is formed on the extracting surface 34 of the first solid immersion lens 31. The first film member 36 transmits the terahertz wave T, and reflects the pulsed laser L1. Because of this, the first film member 36 is capable of preventing the pulsed laser L1 from entering the first solid immersion lens 31. The first film member 36 is thus capable of preventing the first solid immersion lens 31 from generating the terahertz wave T. As a result, the accuracy of detecting the terahertz wave T, which is generated from the object device S, may be increased.

The material of the first film member 36 is, for example, a dielectric material film ($SiO_2$, SiN, etc.), a semiconductor film (Si, GaAs, etc.), a metal film (Al, Cu, etc.), or the like. The first film member 36 may be a single-layer film or a multi-layer film.

The first film member 36 is formed by the following film-forming process. The examples of the film-forming process include vapor deposition, sputtering, and the like. For example, a designer simulates an optical multi-layer thin film based on the wavelength of a pulsed laser to be reflected and based on a predetermined reflectance. Based on the simulation, he designs the film thickness of the first film member 36, the number of the films, and the material. In order that the first film member 36 may not generate the terahertz wave T when the pulsed laser L1 is irradiated on the first film member 36, all the materials should be dielectric materials, ideally. However, what is required is that the amount of the the terahertz wave T, which is generated from the first film member 36, is small. That is, the first film member 36 is not necessarily made of a dielectric material. That is, the S/N ratio of the signal, which the photoconductive device 60 detects, may be determined as long as the terahertz wave T from the object device S, which is supposed to be detected, is detected without any difficulty.

As shown in FIG. 2, the ellipsoidal mirror 33 includes the first opening 37, the reflector surface 38, and the second opening 39. The first opening 37 is at the side of the back surface 18 of the plate 15. The reflector surface 38 surrounds the first and second solid immersion lenses 31 and 32. The second opening 39 is at the side of the entrance surface 64 (see FIG. 4) of the photoconductive device 60. The reflector surface 38 is designed such that the reflector surface 38 is an ellipse having two focal points. In this embodiment, the object device S is arranged on the first focal point 41, i.e., one of the two focal points. The photoconductive device 60 is arranged on the second focal point 42, i.e., the other focal point. Because of this, the terahertz wave T may be guided efficiently from the object device S on the first focal point 41 to the photoconductive device 60 on the second focal point 42.

In this embodiment, a point, on which the semiconductor device 16 contacts the plate 15 and which is approximately at the center of the semiconductor device 16 when the semiconductor device 16 is seen in the direction in which the pulsed laser L1 enters, is on the first focal point 41. Further, the side of the surface 63 (see FIG. 4), on which the electrodes 62 are formed, of the photoconductive device 60 is on the second focal point 42. Because of this, the terahertz wave T, which is generated from the object device S, may be detected with a high degree of accuracy. Note that the points, which are arranged on the first and second focal points 41 and 42, may be adjusted. That is, another point (another part) of the object device S may be on the first focal point 41. Another point (another part) of the photoconductive device 60 may be on the second focal point 42.

In this embodiment, the ellipsoidal mirror 33 has the first focal point 41 and the second focal point. The object device S is on the first focal point 41. The photoconductive device 60 is on the second focal point. The photoconductive device 60 is configured to detect the terahertz wave T, which is extracted by the first solid immersion lens 31. The ellipsoidal mirror 33 guides the extracted terahertz wave T to the photoconductive device 60. That is, the ellipsoidal mirror 33 functions as an ellipsoidal reflector surface.

Further, in this embodiment, the reflector film member 43 is formed on the reflector surface 38 of the ellipsoidal mirror 33. The reflector film member 43 reflects the terahertz wave. Because of this, the efficiency of collecting the terahertz wave T may be increased. The reflector film member 43 may be made of any arbitrary material. The reflector film member 43 may be formed by any processing method. For example, an arbitrary base material is machine-processed or casted. A material, which reflects the terahertz wave T, is coated on the reflector surface 38. Alternatively, the reflector film member 43 may be formed on a part of the reflector surface 38.

Instead of forming the reflector film member 43, the ellipsoidal mirror 33 itself may be made of a material, which reflects the terahertz wave T, such as aluminum, for example. The ellipsoidal mirror 33 made of such a material may be cut, for example. The reflector film member 43 may thus be formed. Also thanks to such a reflector film member 43, the efficiency of collecting the terahertz wave T may be increased. Further, the number of parts may be reduced, the device may be downsized, and the cost may be reduced.

If the reflector film member 43 is not provided, reflection loss may be reduced, and detection accuracy may be increased. Meanwhile, if the reflector film member 43 is provided, restrictions on optical design are eased. As a result, it plays an important role on, for example, downsizing the device.

In this embodiment, the refractive index of the second solid immersion lens 32 is approximately similar to the refractive index of the photoconductive device 60.

The second solid immersion lens 32 is optically coupled with the photoconductive device 60. As a result, the second solid immersion lens 32 collects the terahertz wave T, which is guided by the ellipsoidal mirror 33, on the photoconductive device 60. That is, the second solid immersion lens 32 functions as a light-collecting section.

As shown in FIG. 4, the second solid immersion lens 32 includes the entrance surface 45 and the coupling surface 46. The terahertz wave T, which is guided by the ellipsoidal mirror 33, enters the entrance surface 45. The entrance surface 45 is curved. The coupling surface 46 is adjacent to or abuts on the photoconductive device 60. The coupling surface 46 is flat. The second solid immersion lens 32 may be made of any material. For example, the second solid immersion lens 32 may be made of a semiconductor such as Si or Ge, or a dielectric material such as $Al_2O_3$ or $SiO_2$. The material may be selected arbitrarily such that the refractive index of the terahertz electromagnetic waveband is approximately equal to the refractive index of the photoconductive device 60 (the plate 61).

The second solid immersion lens 32 may have any shape. The second solid immersion lens 32 may be designed arbitrarily. For example, the curved entrance surface 45 may not be a hemisphere. The curved entrance surface 45 may be a part of a hemisphere, aspheric, a fresnel lens, or the like. In this embodiment, the second solid immersion lens 32 has the curved entrance surface 45 and the flat coupling surface 46. Because of this, the second solid immersion lens 32 is capable of collecting the terahertz wave T efficiently.

In this embodiment, the distance between the coupling surface 46 of the second solid immersion lens 32 and the entrance surface 64 of the plate 61 of the photoconductive device 60 is 1 mm or less. Because of this, the second solid immersion lens 32 is capable of collecting the terahertz wave T sufficiently. The distance between the coupling surface 46 and the entrance surface 64 may not be 1 mm or less.

As shown in FIG. 4, the second film member 47 is formed on the entrance surface 45 of the second solid immersion lens 32. The second film member 47 transmits the terahertz wave T, and reflects the pulsed laser L1. Because of this, the second film member 47 is capable of preventing the pulsed laser L1 from entering the second solid immersion lens 32 and the photoconductive device 60. The second film member 47 is thus capable of preventing the second solid immersion lens 32 and the photoconductive device 60 from generating the terahertz wave T. As a result, the accuracy of detecting the terahertz wave T, which is generated from the object device S, may be increased.

The material of the second film member 47 is, for example, a dielectric material film ($SiO_2$, SiN, etc.), a semiconductor film (Si, GaAs, etc.), a metal film (Al, Cu, etc.), or the like. The second film member 47 may be a single-layer film or a multi-layer film. Further, the way to form the second film member 47 is similar to the way to form the first film member 36. The second film member 47 may be formed based on a simulation or the like, for example. Alternatively, the second film member 47 may be formed by another method.

[Operation of Terahertz Emission Microscope]

Figure 5:
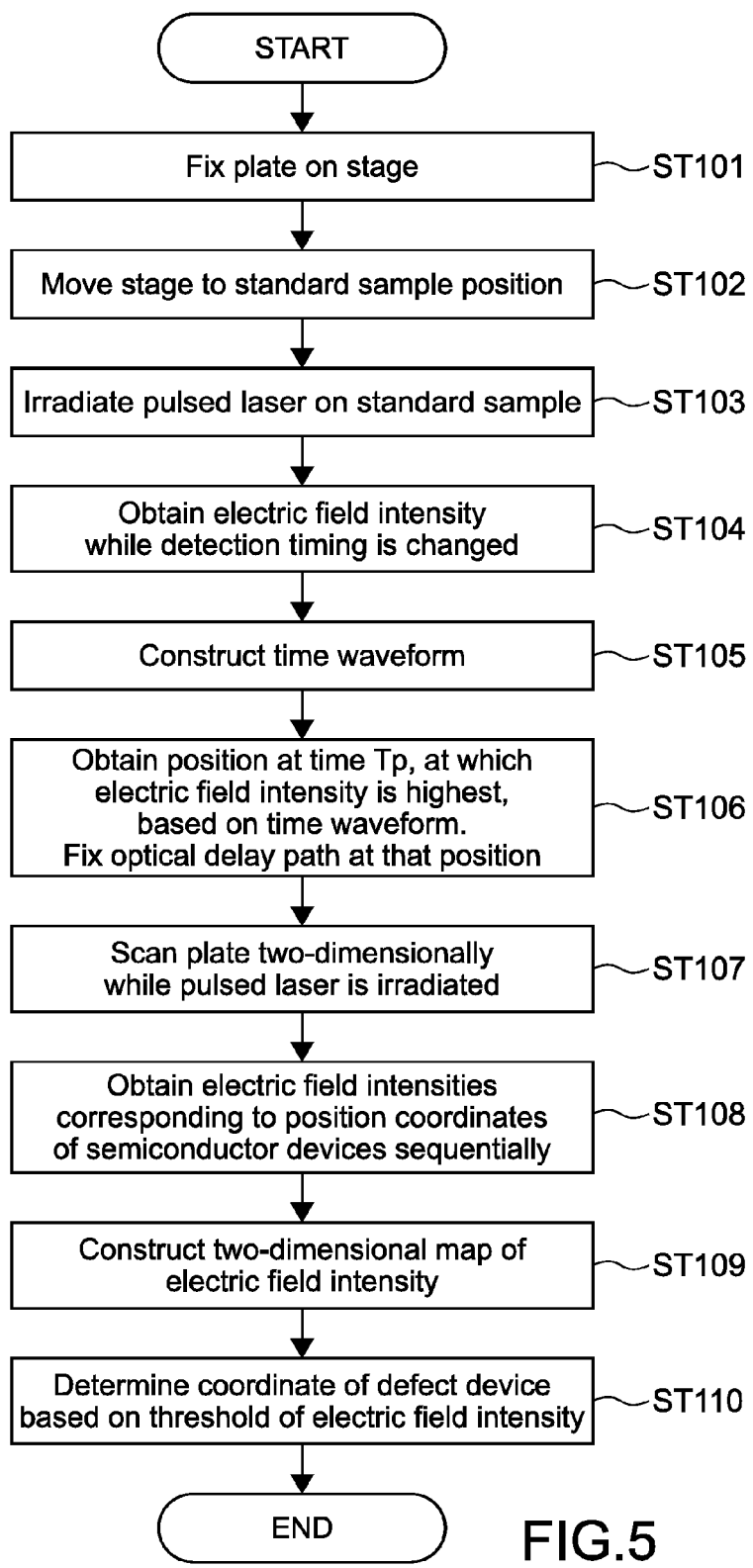
FIG. 5 is a flowchart showing an example of an operation of the terahertz emission microscope.

FIG. 5 is a flowchart showing an example of an operation of the terahertz emission microscope 100. The plate 15 of the object device S is fixed on the stage 70 (Step 101). In this embodiment, a sample is arranged on the plate 15. The sample is a standard of the semiconductor devices 16, i.e., the examined objects. The stage 70 moves to the following position (standard sample position). That is, the standard sample is at a position on which the pulsed laser L1 is irradiated (Step 102). The pulsed laser L1 is irradiated on the standard sample (Step 103). Under irradiation, the single-axis stage of the optical delay path 23 moves. As a result, the electric field intensity is obtained while the detection timing of the photoconductive device 60 is changed (Step 104). A time waveform is constructed (Step 105).

Figure 6:
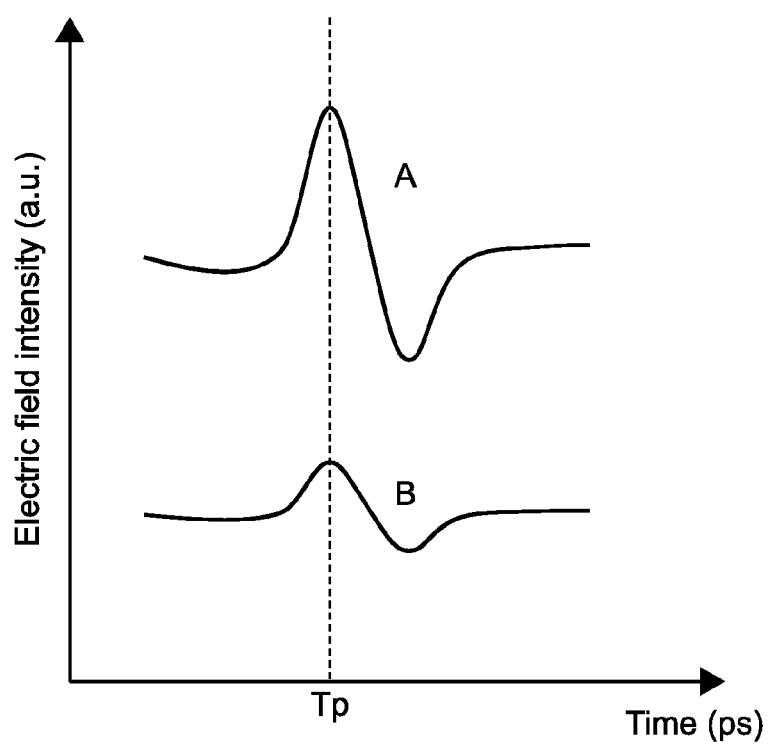
FIG. 6 is a graph schematically showing examples of a time waveform of electric field intensity of a terahertz wave.

FIG. 6 is a graph schematically showing examples of the time waveform. For example, the time waveform A (shown in the upper part of FIG. 6) of a standard sample is obtained. The time waveform A shows a time waveform of a normal device. The time waveform B (shown in the lower part of FIG. 6) of a defect device is obtained. The defect device has a defect inside. The time waveform B shows low electric field intensity. Alternatively, a time waveform, whose electric field intensity is abnormally higher than that of the time waveform A, may be obtained as a time waveform of a defect device. Anyway, it is known that the time waveform of a defect device is different from the time waveform A of the normal device.

The position of the single-axis stage at the time Tp, at which the electric field intensity is the highest, is obtained based on the obtained time waveform A. The single-axis stage of the optical delay path 23 moves to that position. The single-axis stage of the optical delay path 23 is fixed at that position (Step 106). In this situation, the stage 70 moves. The pulsed laser L1 is irradiated on each of the semiconductor devices 16 on the plate 15 in order (Step 107). In this embodiment, the plurality of semiconductor devices 16 are on the plate 15. For example, the number of the semiconductor devices 16 on the plate 15 is n×n (n in height and n in width). Each semiconductor device 16 has its position coordinate. For example, the coordinate of the lower left semiconductor device 16 is (0, 0). The position coordinate of each semiconductor device 16 is set based on this coordinate. The number of the semiconductor devices 16, the way to arrange the semiconductor devices 16, and the way to set coordinates are not limited to the above description.

The electric field intensities of the terahertz wave T at the position coordinates of the semiconductor devices 16 are obtained sequentially. That is, the set coordinate information is associated with information on the electric field intensity. The set coordinate information and the information on the electric field intensity are obtained sequentially (Step 108). The operation at this time may be a so-called step-and-repeat method. The step-and-repeat method includes the following operation, i.e., move, stop, obtain electric field intensity, and move. Alternatively, the operation may be a scan method. In the scan method, electric field intensity is obtained sequentially while the stage 70 moves.

Figure 7:
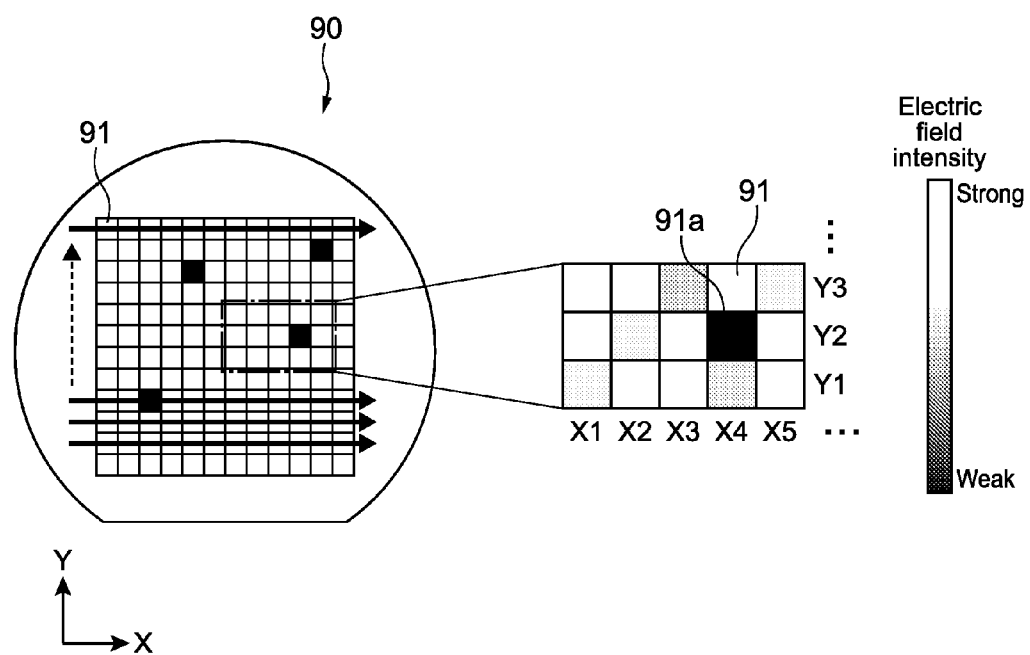
FIG. 7 is a diagram showing an example of the a two-dimensional map of electric field intensity.

A two-dimensional map of the terahertz electric field intensity at the time Tp is constructed based on the obtained information (Step 109). The two-dimensional map corresponds to the position coordinates of the semiconductor devices 16. FIG. 7 is a diagram showing an example of the two-dimensional map 90 of electric field intensity. For example, let's say that the semiconductor devices 16 are scanned laterally from bottom to top, i.e., tier by tier. Then the value of electric field intensity is stored. Here, the electric field intensity value is associated with the coordinate information. In FIG. 7, each square 91 corresponds to each position coordinate. The color of each square 91 corresponds to the obtained electric field intensity value. For example, the smaller the electric field intensity, the darker the color. Such a two-dimensional map 90 is created. As a result, the position coordinate of a defect device, which has smaller electric field intensity, may be obtained (for example, coordinate (x4, y2) of the square 91a).

Note that, in some defect modes, the terahertz electric field intensity of a defect device may be larger than the terahertz electric field intensity of a normal device. In any event, a threshold is determined based on the terahertz electric field intensity of a normal device. Then, the position coordinate of a device, which has too low or too much terahertz electric field intensity, is obtained. Then the device is determined to be a defect device (Step 110).

As described above, according to the light-guiding optical system 30 of this embodiment, the first solid immersion lens 31 is optically coupled with the device S, i.e., the observed object. The first solid immersion lens 31 extracts the terahertz wave T, which is generated from the object device S. Further, the ellipsoidal mirror 33 guides the terahertz wave T from the object device S on the first focal point 41 to the photoconductive device 60 on the second focal point 42. As a result, the efficiency of extracting the terahertz wave T is increased, and the efficiency of collecting the photoconductive device 60 is increased. As a result, the accuracy of detecting the terahertz wave T may be increased.

In a case of detecting the terahertz wave T, inspecting defects, and the like, it is required to detect the terahertz wave T, which is generated from the object device S, with a high degree of accuracy. However, in many cases, the terahertz wave T, which is generated from the object device S, is extremely weak. Therefore it is difficult to detect the terahertz wave T with a high degree of accuracy.

Figure 8A:
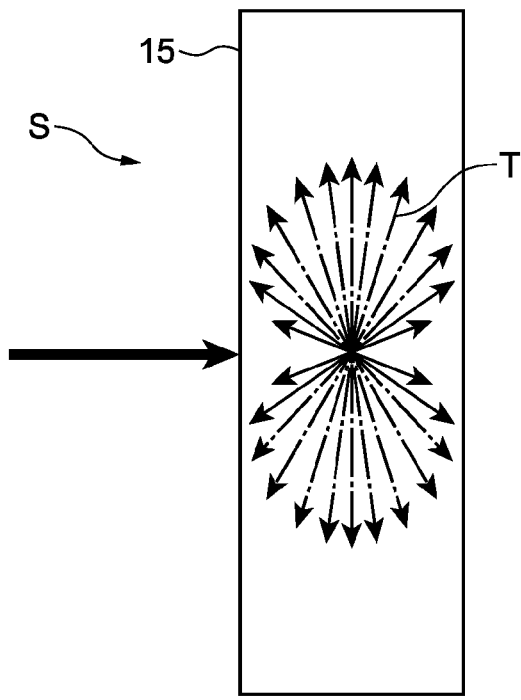
FIGS. 8A and 8B are diagrams schematically showing the paths of the terahertz wave T, which is generated from an object device.
Figure 8B:
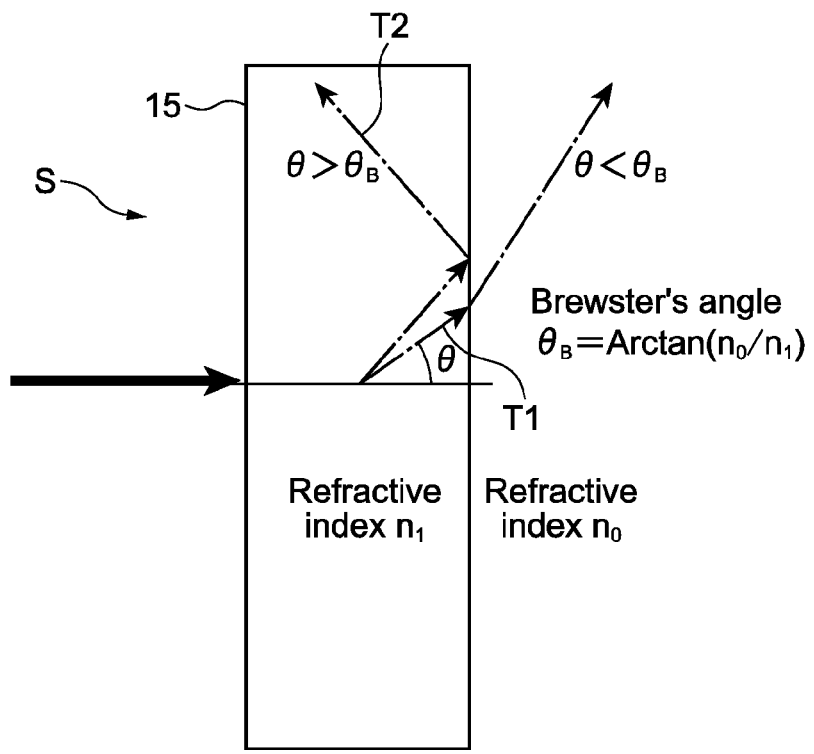

FIGS. 8A and 8B are diagrams schematically showing the paths of the terahertz wave T, which is generated from the object device S. For example, let's say that the object device S is a light-emitting device such as a semiconductor laser or a light-emitting diode. In this case, the device is designed as follows most of the time.

That is, the thickness direction of the device is the same as or is close to the direction of the internal electric field of the p-n junction of the device. Because of this, the direction of dipole moment, which causes terahertz waves, is the same as the device thickness direction. Because of this, almost all of the terahertz waves T, which are radiated from the object device S, are trapped in the plate 15 because of total reflection. That is, as shown in FIG. 8A, the object device S generates the terahertz waves T in all directions. However, as shown in FIG. 8B, only the terahertz wave T1 is radiated to the outside. The incident angle θ of the terahertz wave T1 is smaller than Brewster's angle $\theta_B$. The terahertz wave T2 is trapped. The incident angle θ of the terahertz wave T2 is larger than Brewster's angle $\theta_B$.

Further, let's say that a parabolic mirror is used to collect the terahertz wave T. In this case, the radiation angle, in which the parabolic mirror is capable of collecting the terahertz wave T, is limited to the vicinity of the normal direction of the device. As understood from the above description, an extremely small percentage of the terahertz electromagnetic wave component, which is generated from the object device S, is guided to the photoconductive device. As a result, the accuracy of detecting the terahertz wave T, which is generated from the object device S, is decreased. The S/N ratio is decreased.

A method using a Winstone cone mirror may be used to collect the terahertz wave T in a wider radiation angle. However, the components of terahertz electromagnetic wave, which are reflected in Winstone cone mirror, have different optical paths. Because of this, the terahertz electromagnetic wave pulse at the light-collection position is blurred. As a result, a normal device may sometimes be determined to be a defect device falsely.

According to the terahertz emission microscope 100 of this embodiment, the first solid immersion lens 31 is adjacent to or abuts on the plate 15. Because of this, the first solid immersion lens 31 is capable of extracting the terahertz wave T, which is trapped in the plate 15, sufficiently. That is, it is possible to collect terahertz waves of a wider radiation angle. Further, the ellipsoidal mirror 33 is capable of collecting the extracted terahertz waves T, which have certain optical-path lengths, on the photoconductive device 60 without time lag with a high degree of efficiency. As a result, the accuracy of detecting the terahertz wave T may be increased, and the S/N ratio may be increased.

Further, surrounding terahertz waves are detected simultaneously when the terahertz waves T are detected. The surrounding terahertz waves may cause a noise. The pulsed laser L1 is irradiated on the object device S directly. Because of this, the pulsed laser L1 may be reflected by the object device S, may diffuse in the object device S, may pass through the object device S, and the like. The pulsed laser L1 may enter the light-guiding optical system 30 together with the generated terahertz wave T. Further, the pulsed laser L1 may be irradiated on the first and second solid immersion lenses 31 and 32 and the photoconductive device 60. Let's say that the first and second solid immersion lenses 31 and 32 and the photoconductive device 60 are made of semiconductor materials. In this case, the first solid immersion lens 31, the second solid immersion lens 32, or the photoconductive device 60 generates terahertz waves by themselves because of photo-Dember effect or the like.

When such terahertz wave radiation occurs, it is difficult to remove such terahertz waves from the terahertz wave T, which is generated from an object to be measured. As a result, the S/N ratio is further decreased.

In view of the above-mentioned circumstances, the optical system of the terahertz emission microscope 100 may include a transparent conductive film coating plate, which reflects terahertz waves and transmits ultrashort pulsed laser. However, reflection loss of ultrashort pulsed laser reflected by the transparent conductive film coating plate occurs. Because of this, the S/N ratio is decreased after all in a case where available laser output is limited. This is a problem.

In view of the above-mentioned circumstances, according to the present technology, the first film member 36 is formed on the extracting surface 34 of the first solid immersion lens 31. The first film member 36 transmits the terahertz wave T, and reflects the pulsed laser L1. Further, the second film member 47 is formed on the entrance surface 45 of the second solid immersion lens 32. The second film member 47 transmits the terahertz wave T, and reflects the pulsed laser L1. The first film member 36 and the second film member 47 reflect the pulsed laser L1, which generates unnecessary terahertz waves. As a result, the accuracy of detecting the terahertz wave T generated from the object device S, which is supposed to be detected, may be increased.

Figure 9:
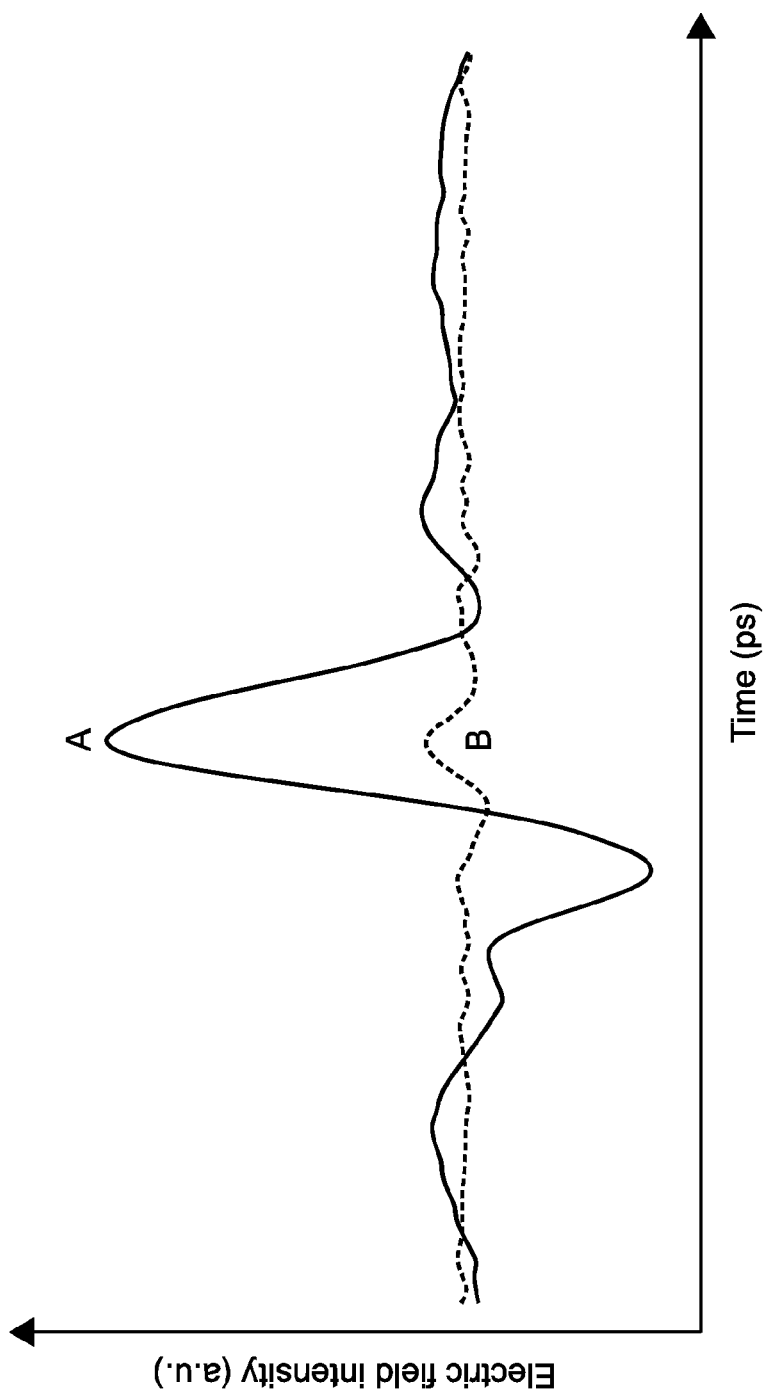
FIG. 9 is a graph showing a time waveform showing terahertz waves, which is detected by the terahertz emission microscope of the present technology, and a time waveform showing terahertz waves, which is detected by an apparatus of a related art.

FIG. 9 is a graph showing the time waveform A and the time waveform B. The time waveform A shows terahertz waves, which is detected by the terahertz emission microscope 100 of the present technology. The time waveform B shows terahertz waves, which is detected by an apparatus of a related art. In the measurement, a titanium-sapphire femtosecond laser (pulse width is 100 ps, repetition frequency is 80 MHz, center wavelength is 800 nm) is used as an ultrashort pulsed laser. Further, a bow-tie antenna photoconductive device (sensitive to frequency of 0.1 THz to 5 THz) is used as a photoconductive device. As shown in FIG. 9, it is understood that the efficiency of collecting terahertz waves is increased greatly according to the present technology.

<Second Embodiment>

The light-guiding optical system according to the second embodiment of the present technology will be described. In the following description, structures and behaviors, which are similar to those of the light-guiding optical system 30 of the above-mentioned embodiment, will not be described or will be simplified.

Figure 10:
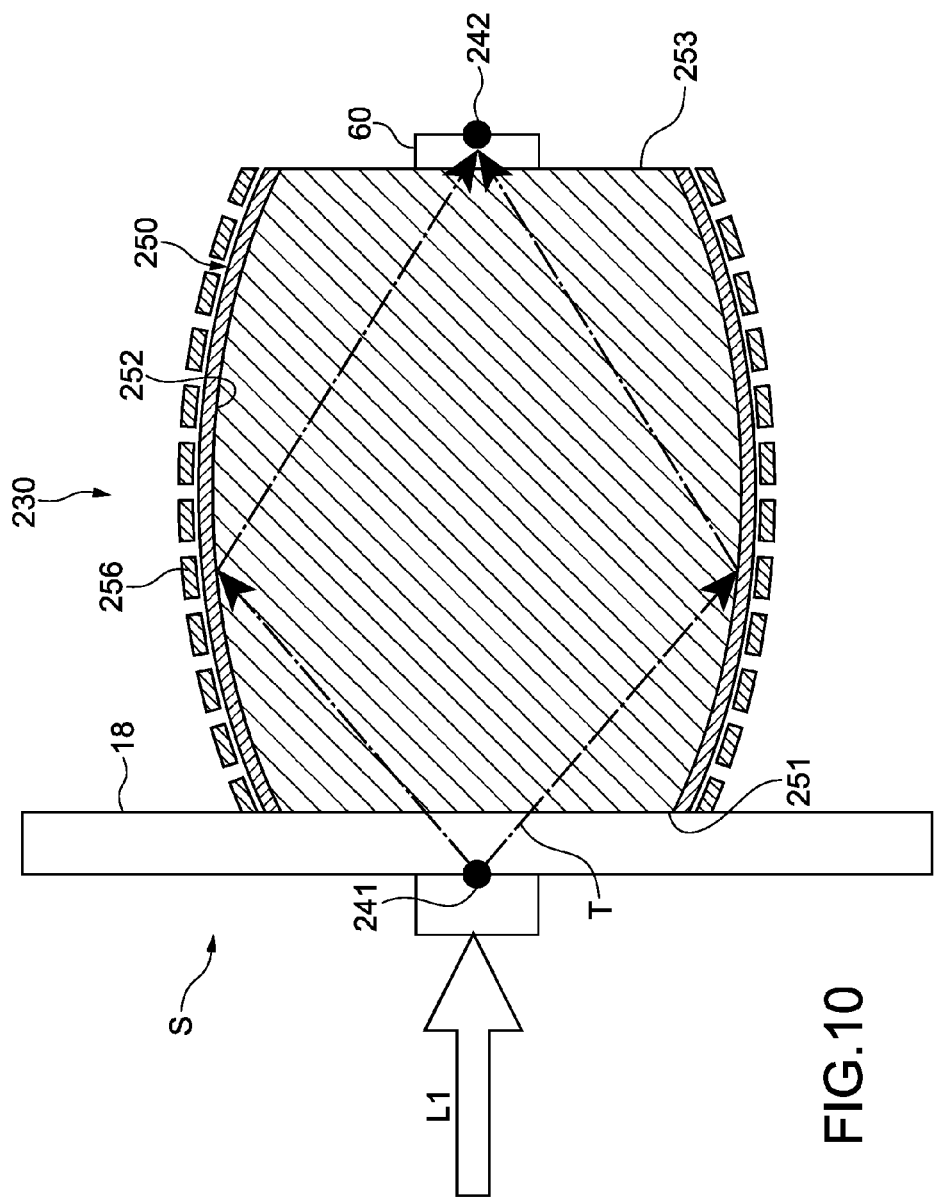
FIG. 10 is a diagram schematically showing the structure of a light-guiding optical system of the second embodiment.
Figure 11:
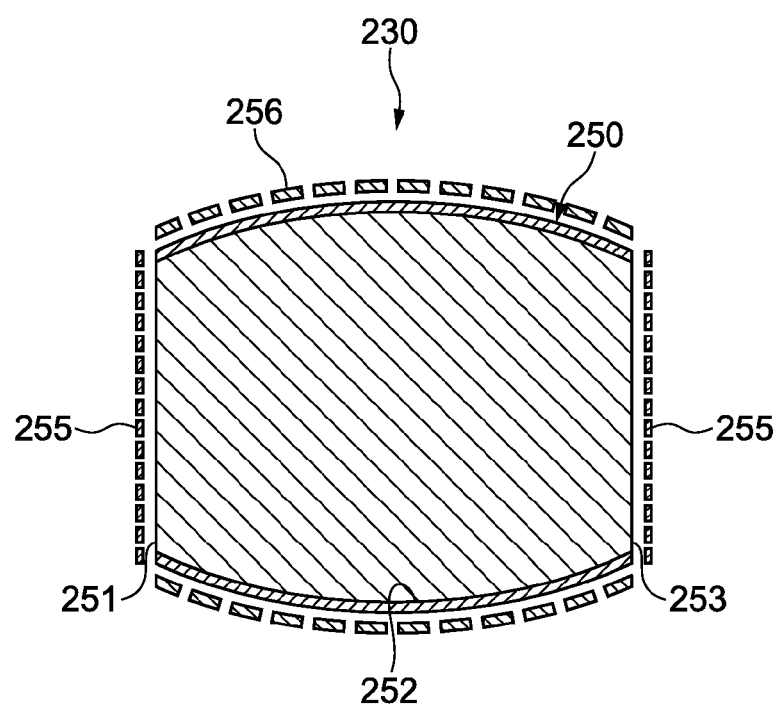
FIG. 11 is a diagram schematically showing the structure of the light-guiding optical system of the second embodiment.

Each of FIG. 10 and FIG. 11 is a diagram schematically showing the structure of the light-guiding optical system 230 of this embodiment. According to the first embodiment, the first solid immersion lens 31 functions as an extracting section. The ellipsoidal mirror 33 functions as an ellipsoidal reflector surface. Further, the second solid immersion lens 32 functions as a light-collecting section. In the second embodiment, as shown in FIG. 10, the ellipsoidal lens 250 functions as an extracting section, an ellipsoidal reflector surface, and a light-collecting section.

The ellipsoidal lens 250 includes the first surface 251 and the second surface 252. The flat first surface 251 is adjacent to or abuts on the back surface 18 of the object device S. The ellipsoidal second surface 252 has the first and second focal points 241 and 242. Further, the ellipsoidal lens 250 includes the third surface 253. The flat third surface 253 is adjacent to or abuts on the photoconductive device 60. The first surface 251 is optically coupled with the object device S. The second surface 252 guides the terahertz wave T from the object device S to the photoconductive device 60. The object device S is on the first focal point 241. The photoconductive device 60 is on the second focal point 242. The third surface 253 is optically coupled with the photoconductive device 60 to collect the terahertz wave T, which is guided by the second surface 252, on the photoconductive device 60. In this embodiment, the third surface 253 functions as a coupling surface.

The ellipsoidal lens 250 may be made of any material, and may be made of a material similar to the above-mentioned material of the first solid immersion lens 31. Typically, the refractive index of the ellipsoidal lens 250 is approximately the same as the refractive index of the object device S. Because of this, the ellipsoidal lens 250 may extract the terahertz wave T sufficiently. Note that the refractive index of the ellipsoidal lens 250 may be approximately the same as the refractive index of the photoconductive device 60 to mainly increase the light-collecting efficiency of the photoconductive device 60. Let's say that the refractive index of the object device S is approximately the same as the refractive index of the photoconductive device 60. In this case, the refractive index of the ellipsoidal lens 250 may be approximately the same as the refractive index of the object device S or the refractive index of the photoconductive device 60. Because of this, the extracting efficiency and the light-collecting efficiency may be increased.

The distance between the first surface 251 of the ellipsoidal lens 250 and the back surface 18 of the object device S is 1 mm or less. Further, the distance between the third surface 253 and the photoconductive device 60 is 1 mm or less. Because of this, the ellipsoidal lens 250 may extract the terahertz wave T sufficiently, and may collect the terahertz wave T on the photoconductive device 60. Note that the distance between the first surface 251 of the ellipsoidal lens 250 and the back surface 18 of the object device S may not be 1 mm or less. The distance between the third surface 253 and the photoconductive device 60 may not be 1 mm or less.

As shown in FIG. 11, the film member 255 is formed on the first surface 251. The film member 255 is formed on the third surface 253. Each film member 255 transmits the terahertz wave T, and reflects the pulsed laser L1. Because of this, it is possible to prevent the pulsed laser L1 from entering the ellipsoidal lens 250, and prevent the ellipsoidal lens 250 and the photoconductive device 60 from generating the terahertz electromagnetic wave. As a result, the accuracy of detecting the terahertz wave T, which is generated from the object device S, may be increased. The material of the film members 255 may be the same as the above-mentioned material of the first and second film members 36 and 47. The way to manufacture the film members 255 may be the same as the above-mentioned way to manufacture the first and second film members 36 and 47. Note that the film member may be formed on any one of the first and third surfaces 251 and 253.

Further, as shown in FIG. 10 and FIG. 11, the reflector film member 256 is formed on the ellipsoidal second surface 252. The reflector film member 256 reflects the terahertz wave T. Because of this, the efficiency of collecting the terahertz wave T may be increased. The reflector film member 256 may be made of any material and may be formed by any method.

As described above, the ellipsoidal lens 250 may function as an extracting section and an ellipsoidal reflector surface. Also according to this structure, the efficiency of extracting the terahertz wave T may be increased. The efficiency of collecting the terahertz wave T may be increased. The detection accuracy may be increased. Further, the light-guiding optical system 230 contains no air. Because of this, decay, which results from fluctuation or moisture of air, may be suppressed. Fresnel reflection loss at the interface between air and the optical device may be suppressed. Other defects may be suppressed. Further, the number of parts may be reduced. The apparatus may be downsized, the cost may be reduced, and the like.

<Third Embodiment>

Figure 12:
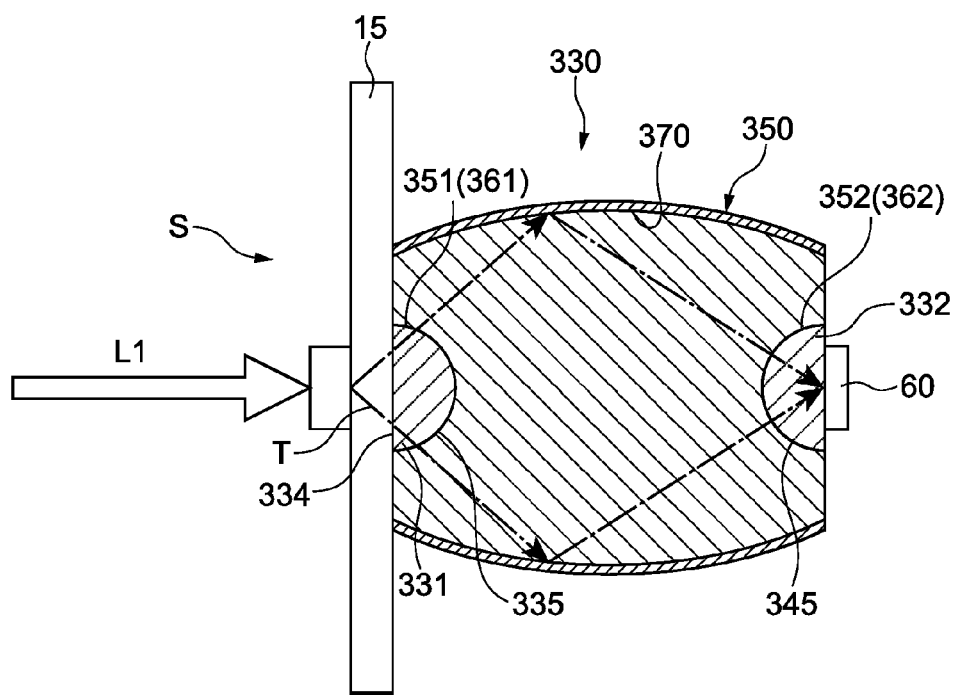
FIG. 12 is a diagram schematically showing the structure of a light-guiding optical system of the third embodiment.

FIG. 12 is a diagram schematically showing the structure of a light-guiding optical system according to the third embodiment of the present technology. The light-guiding optical system 330 includes the first solid immersion lens 331, the ellipsoidal lens 350, and the second solid immersion lens 332. The first and second solid immersion lenses 331 and 332 are similar to those described in the first embodiment.

The ellipsoidal lens 350 includes the first mounting portion 351 and the second mounting portion 352. The first solid immersion lens 331 is mounted in the first mounting portion 351. The second solid immersion lens 332 is mounted in the second mounting portion 352. The concave portion 361 functions as the first mounting portion 351. The curve of the concave portion 361 corresponds to the shape of the output surface 335 of the first solid immersion lens 331. The concave portion 362 functions as the second mounting portion 352. The curve of the concave portion 362 corresponds to the shape of the entrance surface 345 of the second solid immersion lens 332. The two solid immersion lenses are mounted in the concave portions, respectively. As a result, the light-guiding optical system 330 of this embodiment is structured. Note that the structures of the first and second mounting portions 351 and 352 are not limited to the above-mentioned structures. The structures of the first and second mounting portions 351 and 352 may be designed arbitrarily.

The refractive index (first refractive index) of the first solid immersion lens 331 is approximately the same as the refractive index of the plate 15 of the object device S. The refractive index (second refractive index) of the second solid immersion lens 332 is approximately the same as the refractive index of the photoconductive device 60. The refractive index of the ellipsoidal lens 350 may be set arbitrarily. For example, the refractive index of the ellipsoidal lens 350 may be approximately the same as one of the first refractive index and the second refractive index. Alternatively, the refractive index of the ellipsoidal lens 350 may be the intermediate value of the first refractive index and the second refractive index. The refractive index of the ellipsoidal lens 350 may be set arbitrarily as long as the ellipsoidal lens 350 is capable of guiding the terahertz wave T efficiently. Also according to this embodiment, the light-guiding optical system 330 contains no air. Because of this, decay, reflection loss, and the like, which result from air, may be suppressed.

As described above, the first and second solid immersion lenses 331 and 332 and the ellipsoidal lens 350 may be fitted together to structure an extracting section, an ellipsoidal reflector surface, and a light-collecting section. Also thanks to such a structure, the efficiency of extracting the terahertz wave T, the efficiency of collecting the terahertz wave T, and the detection accuracy may be increased.

A reflector film member, which reflects the terahertz wave T, may be formed on the reflector surface 370 of the ellipsoidal lens 350. Further, a film member, which transmits the terahertz wave T and reflects the pulsed laser L1, may be formed on the extracting surface 334 of the first solid immersion lens 331. A film member, which transmits the terahertz wave T and reflects the pulsed laser L1, may be formed on the entrance surface 345 of the second solid immersion lens 332.

<Other Embodiments>

The present technology is not limited to the above-mentioned embodiments. Other various embodiments may be employed.

Figure 13:
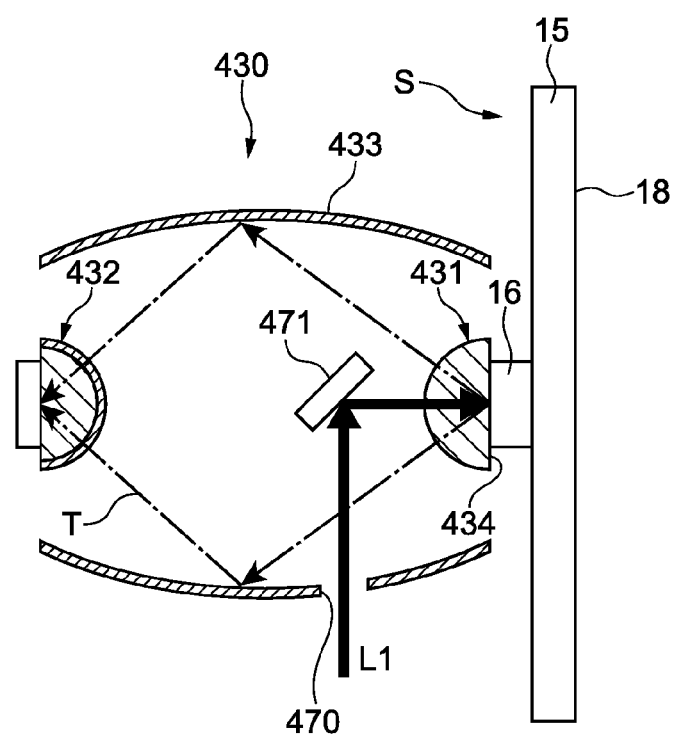
FIG. 13 is a diagram schematically showing the structure of a light-guiding optical system of another embodiment.

FIG. 13 is a diagram schematically showing the structure of a light-guiding optical system of another embodiment. The light-guiding optical system 430 is a kind of modification example of the light-guiding optical system 30 of the first embodiment.

According to the light-guiding optical system 30 of the first embodiment, the first solid immersion lens 31 is at the side of the back surface 18 of the plate 15 of the object device S. The terahertz wave T is extracted at the side of the back surface 18 of the plate 15. Such a structure is appropriate for a case where the terahertz wave T, which is radiated from the semiconductor device 16, is stronger at the plate 15 side. Such a structure is also appropriate for a case where the transmission component of the terahertz wave T is used.

To the contrary, as shown in FIG. 13, the light-guiding optical system 430 may be at the semiconductor device 16 side of the object device S, i.e., the entrance side of the pulsed laser L1. For example, the hole 470 is formed on a part of the ellipsoidal mirror 433. The reflector mirror 471 is provided in the light-guiding optical system 430. The pulsed laser L1 passes through the hole 470, and is irradiated in the light-guiding optical system 430. The reflector mirror 471 reflects the pulsed laser L1. Then, the pulsed laser L1 passes through the first solid immersion lens 431, and is irradiated on the semiconductor device 16. The light-guiding optical system 430 includes the first and second solid immersion lenses 431 and 432, and the ellipsoidal mirror 433. Also thanks to the light-guiding optical system 430 having such a structure, the efficiency of extracting the terahertz wave T, the efficiency of collecting the terahertz wave T, and the detection accuracy may be increased. Note that, according to this embodiment, the extracting surface 434 of the first solid immersion lens 431 needs no film member, which transmits the terahertz wave T and reflects the pulsed laser L1.

The structure of this embodiment is appropriate for a case where the terahertz wave T, which is radiated from the semiconductor device 16, is stronger at the front surface side of the semiconductor device 16. The structure of this embodiment is also appropriate for a case where the reflection component of the terahertz wave T is used. Further, the plate 15 may not transmit the terahertz wave T depending on its material. The light-guiding optical system 430 is also appropriate for such a case.

In the above-mentioned embodiments, the ellipsoidal mirror or the ellipsoidal lens functions as the ellipsoidal reflector surface. The ellipsoidal reflector surface extends from the back surface of the plate to the entrance surface of the photoconductive device. That is, the ellipsoidal reflector surface extends from the extracting surface of the extracting section to the coupling surface of the light-collecting section. The range of the ellipsoidal reflector surface may not be limited to the above-mentioned range. The ellipsoidal reflector surface may be provided in a wider range. For example, the ellipsoidal reflector surface may extend from the front side (entrance side) of the object device to the back side of the photoconductive device.

With this structure, the ellipsoidal reflector surface may collect the terahertz wave, which is the radiation component (reflection component) to the front side of the object device, on photoconductive device. Further, the ellipsoidal reflector surface may reflect the terahertz wave, which travels to the back side of the photoconductive device, to the photoconductive device. The photoconductive device may thus collect the terahertz wave. As a result, a larger amount of terahertz wave may be collected on the photoconductive device. The accuracy of detecting terahertz waves may be increased. Note that a fully-closed ellipsoidal reflector surface may be used alternatively. In this case, for example, a hole or the like may be formed arbitrarily. Then pulsed laser and the sampling pulsed laser L2 may be irradiated through the hole or the like.

In the above-mentioned embodiments, the observed object is a semiconductor device or the like. The present technology is employed to inspect defects in semiconductor devices. The present technology is not limited to this. The present technology may also be employed to inspect various observed objects of other fields. For example, the present technology may be employed in the field of security to inspect food tampering, contents in envelopes and the like, defects inner walls of buildings, and the like. Further, the present technology may not be employed to inspect defects in semiconductor devices as described above. The present technology may be employed in the field of material and biological inspection to inspect biological molecules and the like. The present technology may also be employed in the field of medicine. The observed objects may be biological samples and the like. The present technology may be employed to inspect cancers, to make various diagnoses, and the like. Further, the present technology may also be employed in the field of agriculture to monitor moisture in plants, for example. Further, the present technology may also be employed to inspect forged electronic cards and the like, for example. The present technology may also be employed for any other purpose. For example, the present technology may be employed to collect terahertz electromagnetic waves on a predetermined point to thereby control materials. The present technology may be employed for communication using terahertz electromagnetic waves. The present technology may be employed in other fields.

At least two features of the above-mentioned embodiments may be combined.

Note that the present technology may employ the following structures.

(1) An optical system, comprising:
an extracting section, the refractive index of the extracting section being approximately the same as the refractive index of an observed object, the extracting section being optically coupled with the observed object to thereby extract a terahertz electromagnetic wave generated from the observed object; and
an ellipsoidal reflector surface having a first focal point and a second focal point, the observed object being to be arranged on the first focal point, a photoconductive device being on the second focal point, the photoconductive device being configured to detect the terahertz electromagnetic wave extracted by the extracting section, the ellipsoidal reflector surface guiding the extracted terahertz electromagnetic wave to the photoconductive device.

(2) The optical system according to (1), wherein
the observed object is an observed device.

(3) The optical system according to (2), wherein
the extracting section is a first solid immersion lens, the first solid immersion lens including an extracting surface and an output surface, the extracting surface being flat, the extracting surface being adjacent to or abutting on the device, the output surface being curved, the output surface outputting the extracted terahertz electromagnetic wave, and
the ellipsoidal reflector surface is an ellipsoidal mirror.

(4) The optical system according to any one of (1) to (3), further comprising:
a light-collecting section, the refractive index of the light-collecting section being approximately the same as the refractive index of the photoconductive device, the light-collecting section being optically coupled with the photoconductive device to thereby collect the terahertz electromagnetic wave on the photoconductive device, the terahertz electromagnetic wave being guided by the ellipsoidal reflector surface.

(5) The optical system according to (4), wherein
the light-collecting section is a second solid immersion lens, the second solid immersion lens including an entrance surface and a coupling surface, the entrance surface being curved, the terahertz electromagnetic wave entering the entrance surface, the terahertz electromagnetic wave being guided by the ellipsoidal reflector surface, the coupling surface being flat, the coupling surface being adjacent to or abutting on the photoconductive device.

(6) The optical system according to any one of (3) to (5), wherein
a reflector film member is formed on the ellipsoidal mirror, the reflector film member reflecting the terahertz electromagnetic wave.

(7) The optical system according to any one of (3) to (5), wherein
the ellipsoidal mirror is made of a material reflecting the terahertz electromagnetic wave.

(8) The optical system according to any one of (3) to (7), wherein the extracting section extracts the terahertz electromagnetic wave, the terahertz electromagnetic wave being generated in a case where a pulsed laser is irradiated on the device, and
a first film member is formed on the extracting surface of the first solid immersion lens, the first film member transmitting the terahertz electromagnetic wave and reflecting the pulsed laser.

(9) The optical system according to any one of (5) to (8), wherein
a second film member is formed on the entrance surface of the second solid immersion lens, the second film member transmitting the terahertz electromagnetic wave and reflecting the pulsed laser.

(10) The optical system according to any one of (3) to (9), wherein
the distance between the extracting surface of the first solid immersion lens and the device is 1 mm or less.

(11) The optical system according to any one of (5) to (10), wherein
the distance between the coupling surface of the second solid immersion lens and the photoconductive device is 1 mm or less.

(12) The optical system according to (2), wherein
the extracting section is an ellipsoidal lens, the ellipsoidal lens including a first surface, the first surface being flat, the first surface being adjacent to or abutting on the device, and
the ellipsoidal reflector surface is a second surface of the ellipsoidal lens, the second surface being ellipsoidal.

(13) The optical system according to (12), further comprising:
a coupling surface being optically coupled with the photoconductive device to thereby collect the terahertz electromagnetic wave on the photoconductive device, the terahertz electromagnetic wave being guided by the second surface, the coupling surface being a third surface of the ellipsoidal lens, the third surface being flat, the third surface being adjacent to or abutting on the photoconductive device.

(14) The optical system according to (12) or (13), wherein
a reflector film member is formed on the second surface, the reflector film member reflecting the terahertz electromagnetic wave.

(15) The optical system according to any one of (12) to (14), wherein
the extracting section extracts the terahertz electromagnetic wave, the terahertz electromagnetic wave being generated in a case where a pulsed laser is irradiated on the device, and
a film member is formed on the first surface, the film member transmitting the terahertz electromagnetic wave and reflecting the pulsed laser.

(16) The optical system according to any one of (13) to (15), wherein
the distance between the first surface and the device is 1 mm or less, and
the distance between the third surface and the photoconductive device is 1 mm or less.

(17) The optical system according to (2), wherein
the extracting section includes a first solid immersion lens, the first solid immersion lens including an extracting surface and an output surface, the extracting surface being flat, the extracting surface being adjacent to or abutting on the device, the output surface being curved, the output surface outputting the extracted terahertz electromagnetic wave, the ellipsoidal reflector surface being an ellipsoidal surface of an ellipsoidal lens, the ellipsoidal lens including a first mounting portion, the first solid immersion lens being mounted on the first mounting portion.

(18) The optical system according to (17), further comprising:
a second solid immersion lens, the second solid immersion lens including an entrance surface and a coupling surface, the terahertz electromagnetic wave entering the entrance surface, the terahertz electromagnetic wave being guided by the ellipsoidal surface, the coupling surface being flat, the coupling surface being adjacent to or abutting on the photoconductive device, the second solid immersion lens being mounted on a second mounting portion, the second mounting portion being formed on the ellipsoidal lens.

(19) The optical system according to (18), wherein
the first refractive index of the first solid immersion lens is approximately the same as the refractive index of the device, and
the second refractive index of the second solid immersion lens is approximately the same as the refractive index of the photoconductive device.

(20) A terahertz emission microscope, comprising:
a light source configured to generate a pulsed laser;
a photoconductive device configured to detect a terahertz electromagnetic wave, the terahertz electromagnetic wave being generated in a case where the pulsed laser is irradiated on an observed object;
an extracting section, the refractive index of the extracting section being approximately the same as the refractive index of the observed object, the extracting section being optically coupled with the observed object to thereby extract a terahertz electromagnetic wave generated from the observed object; and
an ellipsoidal reflector surface having a first focal point and a second focal point, the observed object being to be arranged on the first focal point, the photoconductive device being on the second focal point, the ellipsoidal reflector surface guiding the extracted terahertz electromagnetic wave to the photoconductive device.

(21) The terahertz emission microscope according to (20), wherein
the light source is configured to irradiate the pulsed laser on the observed object, whereby the observed object generates a terahertz electromagnetic wave having a frequency of 1010 (Hz) or more and 1014 (Hz) or less. (22) The terahertz emission microscope according to (20) or (21), wherein
the light source is configured to generate a pulsed laser having a wavelength of 2 μm or less and having a pulse width of 100 ps or less.

It should be understood by those skilled in the art that various modifications, combinations, sub-combinations and alterations may occur depending on design requirements and other factors insofar as they are within the scope of the appended claims or the equivalents thereof.

What is claimed is:

1. An optical system, comprising:
   an extracting section, a refractive index of the extracting section being approximately the same as a refractive index of an observed object, the extracting section being optically coupled with the observed object to thereby extract a terahertz electromagnetic wave generated from the observed object; and
   an ellipsoidal reflector surface having a first focal point and a second focal point, the observed object being arranged on the first focal point, a photoconductive device being on the second focal point, the photoconductive device being configured to detect the terahertz electromagnetic wave extracted by the extracting section, the ellipsoidal reflector surface guiding the extracted terahertz electromagnetic wave to the photoconductive device.

2. The optical system according to claim 1, wherein the observed object is an object device.

3. The optical system according to claim 2, wherein:
   the extracting section is a first solid immersion lens, the first solid immersion lens including an extracting surface and an output surface, the extracting surface being flat, the extracting surface being adjacent to or abutting on the object device, the output surface being curved, the output surface outputting the extracted terahertz electromagnetic wave, and
   the ellipsoidal reflector surface is an ellipsoidal mirror.

4. The optical system according to claim 3, wherein a reflector film member is formed on the ellipsoidal mirror, the reflector film member reflecting the terahertz electromagnetic wave.

5. The optical system according to claim 3, wherein the ellipsoidal mirror is made of a material reflecting the terahertz electromagnetic wave.

6. The optical system according to claim 3, wherein:
   the extracting section extracts the terahertz electromagnetic wave, the terahertz electromagnetic wave being generated in a case where a pulsed laser is irradiated on the object device, and
   a first film member is formed on the extracting surface of the first solid immersion lens, the first film member transmitting the terahertz electromagnetic wave and reflecting the pulsed laser.

7. The optical system according to claim 3, wherein the distance between the extracting surface of the first solid immersion lens and the object device is 1 mm or less.

8. The optical system according to claim 2, wherein:
   the extracting section is an ellipsoidal lens, the ellipsoidal lens including a first surface, the first surface being flat, the first surface being adjacent to or abutting on the object device, and
   the ellipsoidal reflector surface is a second surface of the ellipsoidal lens, the second surface being ellipsoidal.

9. The optical system according to claim 8, further comprising a coupling surface being optically coupled with the photoconductive device to thereby collect the terahertz electromagnetic wave on the photoconductive device, the terahertz electromagnetic wave being guided by the second surface, the coupling surface being a third surface of the ellipsoidal lens, the third surface being flat, the third surface being adjacent to or abutting on the photoconductive device.

10. The optical system according to claim 8, wherein a reflector film member is formed on the second surface, the reflector film member reflecting the terahertz electromagnetic wave.

11. The optical system according to claim 8, wherein:
    the extracting section extracts the terahertz electromagnetic wave, the terahertz electromagnetic wave being generated in a case where a pulsed laser is irradiated on the object device, and
    a film member is formed on the first surface, the film member transmitting the terahertz electromagnetic wave and reflecting the pulsed laser.

12. The optical system according to claim 2, wherein the extracting section includes a first solid immersion lens, the first solid immersion lens including an extracting surface and an output surface, the extracting surface being flat, the extracting surface being adjacent to or abutting on the object device, the output surface being curved, the output surface outputting the extracted terahertz electromagnetic wave, the ellipsoidal reflector surface being an ellipsoidal surface of an ellipsoidal lens, the ellipsoidal lens including a first mounting portion, the first solid immersion lens being mounted on the first mounting portion.

13. The optical system according to claim 1, further comprising a light-collecting section, a refractive index of the light-collecting section being approximately the same as the refractive index of the photoconductive device, the light-collecting section being optically coupled with the photoconductive device to thereby collect the terahertz electromagnetic wave on the photoconductive device, the terahertz electromagnetic wave being guided by the ellipsoidal reflector surface.

14. The optical system according to claim 13, wherein the light-collecting section is a second solid immersion lens, the second solid immersion lens including an entrance surface and a coupling surface, the entrance surface being curved, the terahertz electromagnetic wave entering the entrance surface, the terahertz electromagnetic wave being guided by the ellipsoidal reflector surface, the coupling surface being flat, the coupling surface being adjacent to or abutting on the photoconductive device.

15. The optical system according to claim 14, wherein a second film member is formed on the entrance surface of the second solid immersion lens, the second film member transmitting the terahertz electromagnetic wave and reflecting the pulsed laser.

16. The optical system according to claim 14, wherein the distance between the coupling surface of the second solid immersion lens and the photoconductive device is 1 mm or less.

17. A terahertz emission microscope, comprising:
a light source configured to generate a pulsed laser;
a photoconductive device configured to detect a terahertz electromagnetic wave, the terahertz electromagnetic wave being generated in a case where the pulsed laser is irradiated on an observed object;
an extracting section, the refractive index of the extracting section being approximately the same as the refractive index of the observed object, the extracting section being optically coupled with the observed object to thereby extract a terahertz electromagnetic wave generated from the observed object; and
an ellipsoidal reflector surface having a first focal point and a second focal point, the observed object being to be arranged on the first focal point, the photoconductive device being on the second focal point, the ellipsoidal reflector surface guiding the extracted terahertz electromagnetic wave to the photoconductive device.

18. The terahertz emission microscope according to claim 17, wherein
the light source is configured to irradiate the pulsed laser on the observed object, whereby the observed object generates a terahertz electromagnetic wave having a frequency of 1010 (Hz) or more and 1014 (Hz) or less.

19. The terahertz emission microscope according to claim 17, wherein
the light source is configured to generate a pulsed laser having a wavelength of 2 μm or less and having a pulse width of 100 ps or less.

20. A method of manufacturing a device, the method including inspecting a defect in the device by using a terahertz emission microscope, the method comprising:
generating a pulsed laser from a light source;
optically coupling an extracting section with the device to thereby extract the terahertz electromagnetic wave generated from the device, the refractive index of the extracting section being approximately the same as the refractive index of the device;
guiding, by an ellipsoidal reflector surface, the extracted terahertz electromagnetic wave from the device to a photoconductive device, the ellipsoidal reflector surface having a first focal point and a second focal point, the device being on the first focal point, the photoconductive device being on the second focal point; and
detecting, by the photoconductive device, the terahertz electromagnetic wave.

\* \* \* \* \*